United States Patent [19]

Stoltz

[11] Patent Number: 5,902,789
[45] Date of Patent: May 11, 1999

[54] NASAL ADMINISTRATION OF DRUGS

[75] Inventor: Edwin I. Stoltz, Stoughton, Mass.

[73] Assignee: Fisons Corporation, Rochester, N.Y.

[21] Appl. No.: 08/451,137

[22] Filed: May 26, 1995

Related U.S. Application Data

[63] Continuation of application No. 08/277,665, Jul. 20, 1994, abandoned, which is a continuation of application No. 07/919,985, Jul. 27, 1992, abandoned, which is a continuation of application No. 07/396,734, Aug. 18, 1989, abandoned, which is a continuation of application No. 06/855,114, Apr. 23, 1986, abandoned.

[51] Int. Cl.$^6$ ................................................. A61K 38/28
[52] U.S. Cl. ......................................... 514/4; 514/3; 514/2
[58] Field of Search .............................. 514/4, 3, 2

[56] References Cited

U.S. PATENT DOCUMENTS

| | | | |
|---|---|---|---|
| 4,153,689 | 5/1979 | Hirai et al. ................................. | 514/3 |
| 4,166,132 | 8/1979 | Kraska .................................... | 424/330 |
| 4,262,021 | 4/1981 | Kraska .................................... | 514/631 |
| 4,291,060 | 9/1981 | Kraska .................................... | 514/631 |
| 4,308,272 | 12/1981 | Wierenga et al. ......................... | 514/321 |
| 4,315,925 | 2/1982 | Hussain et al. .......................... | 514/177 |
| 4,383,993 | 5/1983 | Hussain et al. .......................... | 424/239 |
| 4,388,457 | 6/1983 | Pettit ...................................... | 536/4.1 |
| 4,414,205 | 11/1983 | Pettit ...................................... | 424/177 |
| 4,423,040 | 12/1983 | Rejadhyaksha ......................... | 424/180 |
| 4,424,210 | 1/1984 | Rajadhyaksha ......................... | 424/180 |
| 4,454,140 | 6/1984 | Goldberg et al. ........................ | 514/289 |
| 4,460,589 | 7/1984 | Wierenga et al. ......................... | 544/321 |
| 4,462,983 | 7/1984 | Azria et al. ............................... | 424/45 |
| 4,476,116 | 10/1984 | Anik ........................................ | 424/177 |
| 4,543,248 | 9/1985 | Stringfellow et al. .................... | 514/272 |
| 4,548,814 | 10/1985 | Rinehart, Jr. ............................. | 424/95 |
| 4,556,557 | 12/1985 | Reichert .................................. | 424/94 |
| 4,560,774 | 12/1985 | Pettit et al. .............................. | 514/450 |
| 4,593,096 | 6/1986 | Wierenga et al. ......................... | 544/321 |
| 4,613,500 | 9/1986 | Suzuki et al. ............................ | 514/15 |
| 4,783,441 | 11/1988 | Thurow ................................... | 514/3 |
| 4,839,341 | 6/1989 | Massey et al. ........................... | 514/3 |

FOREIGN PATENT DOCUMENTS

| | | |
|---|---|---|
| 0 115 627 | 8/1984 | European Pat. Off. . |
| 0 160 501 | 11/1985 | European Pat. Off. . |
| 0 200 383 | 12/1986 | European Pat. Off. . |
| 1 527 605 | 8/1975 | United Kingdom . |
| WO 83/00288 | 2/1983 | WIPO . |

OTHER PUBLICATIONS

*Merck Index*, 10th Edition, p. 957.
*Merck Index*, 10th Edition, p. 1095.
*Kirk–Othmer Encyclopedia of Chemical Technology*, 3rd Edition, vol. 22, pp. 335, 370 and 372.
Hirai et al., "Mechanisms For The Enhancement Of The Nasal Absorption Of Insulin By Surfactants", *International Journal Of Pharmaceutics*, 9: 173–174 (1981).
Salzman et al, The New England Journal of Medicine, vol. 312 (17), pp. 1078–1084, (Apr. 25, 1985).

*Primary Examiner*—Ponnathapura Achutamurthy
*Assistant Examiner*—T. D. Wessendorf
*Attorney, Agent, or Firm*—Linda M. Buckley

[57] ABSTRACT

Compositions and methods for the nasal administration of drugs with reduced nasal irritation are disclosed.

7 Claims, No Drawings

NASAL ADMINISTRATION OF DRUGS

This is a continuation of application(s) Ser. No. 08/277,665, filed on Jul. 20, 1994, now abandoned, which is a continuation appln. of U.S. appln. Ser. No. 07/919,985, filed on Jul. 27, 1992, now abandoned, which is a continuation appln. of U.S. appln. Ser. No. 07/396,734, filed Aug. 18, 1989, now abandoned, which is a continuation appln. of U.S. appln. Ser. No. 06/855,114, filed Apr. 23, 1986, now abandoned.

FIELD OF THE INVENTION

This invention pertains to compositions and methods for the nasal administration of drugs and, particularly, to the nasal administration of water soluble drugs.

BACKGROUND OF THE INVENTION

Many drugs are administered by injection because other methods of administration do not provide acceptable drug delivery. Many drugs, such as insulin, cannot be taken orally because they are inactivated in the digestive track. For example, insulin has been administered traditionally by subcutaneous injection in order to attain the needed drug bioavailability. One disadvantage of subcutaneous drug administration is that many patients are reluctant or unable to give themselves infections several times a day. Other disadvantages of subcutaneously injected drugs, include great intraindividual variability of absorption (See e.g., Berger, M. et al., in Sayler, J. S. ed. *Insunn. update:* 1982 *Amersterdam Excerpta Medica,* 1982, 97–110; Galoway, J. A. et al., *Diabetes Care* (1981), 4:366–76) and absorption at too slow a rate to provide rapid onset and short duration of drug action. Nasal administration of drugs offers advantages over subcutaneous administration in terms of rate of absorption as well as of convenience. Thus, the nasal route for drug administration is of great interest.

Drugs are often poorly absorbed through the nasal mucosa and thus administration by, e.g., a nasal spray, typically requires larger amounts of the drug than administration by injection. Various methods have been tried to enhance absorption of drugs across nasal membranes. For example, U.S. Pat. No. 4,476,116 discloses polypeptide containing pharmaceutical formulations having chelating agents which enhance peptide absorption across nasal mucous membranes.

Several investigators have demonstrated that insulin can be delivered across the nasal mucosa in biologically active doses (Major, R. H., *J. Lab. Clin. Med.* (1935), 2, 278–80; Hanxiss J. et al., *Acta. Med. Acad. Sci. Hung* (1958), 12, 107–14; Hirai S. et al., *Diabetes* (1978), 27, 296–9; Hirata Y. et al., Amsterdam: Excerpta Medica International Congress Semes. 1979, 468, 319–26; Pondroli A. E. et al., *Br. Med. J.* (1982) 284, 303–6; Moses, A. C. et al., *Diabetes* (1983) 32, 1040–7). Aside from its convenience, nasally administered insulin is absorbed rapidly by the nasal mucosa, mimicking more closely the insulin response to a meal seen in normal persons.

Compositions which can be utilized to improve the absorption of nasally administered drugs with reduced nasal irritation, especially when used with chronically administered drugs, are desirable.

The utilization of certain surface-active agents to enhance the absorption of insulin has been demonstrated. Hirai and coworkers (Hirai, S. et *Intl. J. Pharmaceutics* (1981) 1, 173–184; G.B. Patent specification 1 527 605) have shown enhanced absorption of nasally administered insulin in rats by the use of surface-active agents such as laureth-9. Salzman and coworkers have demonstrated enhanced absorption of nasally administered insulin in humans using laureth-9 (Salzman, R. et al., *N.E. J. Medicine,* 1985 April, 1078–1084) but found that such administration was often accompanied by nasal irritation such as stinging, congestion and rhinorrhea, predominantly due to the surfactant laureth-9, and that such effects were proportional to the concentration of laureth-9.

Although laureth-9 administered nasally at 0.1% by weight, was tolerated by all subjects tested by Salzman (Salzman et al., supra), it was found that 0.1% laureth-9 was only moderately effective in promoting insulin absorption.

Thus, although intranasal administration of drugs is a potentially useful method of administration, compositions which enhance absorption through the nasal mucosa with reduced irritation are desirable.

SUMMARY OF THE INVENTION

In accord with the present invention compositions and methods for nasal delivery of drugs are provided by using a combination of surfactants. Use of such compositions provides superior absorption of drugs through the nasal mucosa with reduced nasal irritation.

DETAILED DESCRIPTION OF THE INVENTION

It was unexpectedly found that polysorbate-80 reduces the irritation caused by intranasally administered drugs wherein absorption of the drug is enhanced by use of nonionic surfactants. Polysorbate-80 has traditionally been used for its key functional properties of emulsification and solubilizing power (*Encyclopedia of Chemical Terminology* (3rd ed.) 22: 335, 372, Wiley-Interscience). Polysorbate-80 is used as an emulsifier and dispersing agents for medicinal products designed for internal use (The Merck Index, 10th ed., Entry 7455).

Compositions for intranasal delivery of drugs with reduces irritation according to the present invention comprise the drug or drugs to be delivered, at least one nonionic surfactant which enhances drug absorption across the nasal mucosa and polysorbate-80.

Compositions according to the present invention are preferably administered from solution as a nasal spray and may be dispensed as a spray by a variety of methods known to those skilled in the art. Preferred systems for dispensing liquids as a spray are disclosed in U.S. Pat. No. 4,511,069. Such systems were used in carrying out the work described in the examples set forth hereinafter. Such nasal spray solutions comprise the drug or drug to be delivered, a nonionic surfactant which enhances absorption of the drug, polysorbate-80, and one or more buffers. In some embodiments of the present invention, the nasal spray solution further comprises a propellant. The pH of the nasal spray solution is preferably between pH 6.8 and 7.2.

Nonionic surfactants such as nonoxynol-9, laureth-9, poloxamer-124, octoxynol-9 and lauramide DEA are useful in the practice of the present invention. Nonoxynol-9 ("N-9") has been found to be particularly useful for intranasal administration of insulin.

N-9 is an ethoxylated alkyl phenol, the polyethyleneoxy condensate of nonylphenol with 9 mols of ethylene oxide. This surfactant has been used in detergent products and is sold under trade names, such as, Surfonic N-95 (Jefferson), Neutronyx 600 (Onyx) and Igepal CO-630 (GAF). N-9 is considered to be a hard detergent. N-9 has also been used as a spermatocide (The Merck Index, 10th Edition, Entry 6518).

In compositions according to the present invention, the nonionic surfactant is preferably present at a concentration of from 0.05 to 0.9% by weight and polysorbate-80 is preferably present at a concentration of from 0.01 to 0.5% by weight. An especially preferred composition comprises 0.5% by weight of a solution that is 10:90 polysorbate 80:N-9 wt:wt to yield a final concentration of 0.05% polysorbate-80 and 0.45% N-9 by weight.

Drugs which can be administered nasally by use of compositions according to the present invention will be readily apparent to those skilled in the art. Water soluble drugs such as peptides and steroids are particularly suited for intranasal administration using the compositions and methods of the present invention. Peptides which can be intranasally administered according to the present invention include insulin, cholecystokinin ("CKK"), lutenizing hormone releasing hormone ("LHRH") and analogs thereof somastostatin and analogs thereof and atrial natriuretic factor ("ANF") and analogs thereof. Steroids which can be intranasally administered according to the present invention include female sex steroids, glucocorticoids and mineralocorticoids.

The desired concentration of the drug or drugs in compositions according to the present invention, can be readily determined by those skilled in the art of pharmacology. Compositions according to the present invention for the nasal administration of insulin are preferably effective in reducing blood glucose levels by from about 40% to 60% of the pre-dose blood glucose level within 45 to 60 minutes.

Nasal spray solutions of the present invention, comprise the drug or drugs to be administered, a nonionic surfactant which enhances nasal absorption of the drug and polysorbate-80, together with one or more pharmaceutically acceptable carriers therefor and optionally other therapeutic ingredients. The carrier(s) must be "acceptable" in the sense of being compatible with the other ingredients of the formulation and not deleterious to the recipient thereof. Such carriers are well known to those skilled in the art of pharmacology. Desirably, the formulation should not include oxidizing agents and other substances with which the drug(s) to be administered are known to be incompatible. The formulations may be prepared by any of the methods well known in the art of pharmacy. All methods according to the present invention include the step of bringing into association the drug or drugs to be delivered, a nonionic surfactant which enhances absorption of the drug, and polysorbate-80 with the carrier which may constitute one or more accessory ingredients. In general, the formulations are prepared by uniformly and intimately bringing into association the nonionic surfactant, polysorbate-80 and drug.

Formulations according to the present invention suitable for nasal administration of drugs conveniently comprise sterile aqueous solutions of the drug or drugs to be administered, a nonionic surfactant which enhances absorption of the drug and polysorbate-80, which solutions are preferably in the range of pH 6.8 to 7.2. Such formulations may be conveniently prepared by dissolving compositions according to the present invention in water to produce an aqueous solution, and rendering said solution sterile. The formulations may be presented in multi-dose containers, for example in the sealed dispensing system disclosed in U.S. Pat. No. 4,511,069.

Various irritation studies have been carried out to determine the effect on nasal irritation of the addition of varying amounts of polysorbate-80 to nasal spray solutions containing the drug to be delivered and a nonionic surfactant to promote absorption of the drug. It was found, for example, that although administration of a nasal spray solution containing insulin and 0.75% by weight of the surfactant nonoxynol-9 produced acceptable blood glucose level reduction, the subject reported nasal irritation and stinging. When the formulation of the nasal spray solution included 0.75% by weight of a solution of polysorbate-80/ nonoxynol-9 (10:90, wt:wt) the subject reported no nasal irritation and blood glucose level reduction was comparable.

Chronic irritation studies, i.e., longer than 5 days, using polysorbate-80 according to the present invention have also been carried out. These studies show that the addition of polysorbate-80 to the nasal spray solution reduces chronic irritation.

The invention will be further understood with reference to the following examples which are purely exemplary in nature and are not meant to be utilized to limit the scope of the invention. In the examples, unless otherwise noted, percentages are by weight. Polysorborate-80 is sometimes designated P-80 and nonoxynol-9 is sometimes designated N-9. Blood Glucose Reduction is designated BGR.

EXAMPLE I (A) A metabolic study was carried out on three normal fasting volunteers. Each group received insulin at 1 U/kg body weight administered nasally from a spray solution comprising 0.1%, 0.25% or 0.75% N-9. Each subject reported nasal irritation in terms of initial stinging and congestion.

(B) A similar metabolic study was carried out on ten fasting normal subjects. Each subject received insulin at 1 U/kg body weight administered nasally from a spray solution comprising 0.5% of a solution of P-80:N-9, 1:3, (a final concentration of 0.125% P-80 and 0.385% N-9). Two out of the ten subjects reported minor congestion.

EXAMPLE II

Irritation Studies

Studies were carried out to determine the effect on nasal irritation of the addition of varying amounts of polysorbate-80 to nasal spray solutions containing N-9. The spray solution in these irritation studies did not contain insulin. In each study ten normal subjects were treated with one squirt (about 0.15 ml) of the nasal spray solution three times a day for ten consecutive days. After administration, the subjects were questioned about any symptoms and findings recorded. The nasal passages were examined on the fifth and tenth days of treatment by an ENT (eyes, nose and throat) specialist and findings recorded.

The nasal spray solutions used in the study comprised 1% of a mixture of polysorbate-80:N-9, 1:9, wt:wt; 0.5% of a mixture of polysorbate-80:N-9, 1:9, wt:wt; 0.25% of a mixture of polysorbate-80:N-9, 1:9, wt:wt; 1% of a mixture of polysorbate-80:N-9, 1:3, wt:wt; 0.5% of a mixture of polysorbate-80:N-9, 1:3, wt:wt; 0.25% of a mixture of polysorbate-80:N-9, 1:3, wt:wt; 0.1% N-9 or a saline placebo. All of the nasal spray solutions produced minor changes in nasal mucosa and minor symptomatic complaints but the number encountered with 0.5% P-80:N-9, 1:9, and 0.5% P-80:N-9:1:3 (4 out of 10 subjects in each group) most closely paralleled the saline placebo (7 out of 20 subjects).

It was found that the fewest number of symptomatic complaints occurred in the 0.5% P-80:N-9,1:3 (final concentration of 0.125% P-80 and 0.375% N-9) group (o subjects), followed by 2 subjects each in the 0.5% P-80:N-9, 1:9 and 0.25% P-80:N-9, 1:9 groups. The fewest number of ENT findings were observed in the 0.5% P-80:N-9 (1:3) group (3 subjects). It was also found that with both the 0.5% P-80:N-9 (1:9) and (1:3) groups no subject had both ENT findings and symptomatic complaints.

Of the group who received pure N-9 at a final concentration of 0.1%, 3 reported symptomatic complaints and 3 ENT findings were observed. One subject had both symptomatic complaints and ENT findings.

EXAMPLE III

The aerosol nasal spray solution of insulin used in this example contained commercially available regular porcine insulin (Eli Lilly) 0.1M $NaH_2PO_4$-$H_2O$ buffer, and varying concentrations of polysorbate-80 and nonoxynol-9. Stock solutions containing 10:90, 50:50 and 25:75 (wt:wt) polysorbate 80: nonoxynol-9 were prepared and added to the spray solution to a final concentration of 0.1% to 0.75% by weight. Nitrous oxide (Union Carbide, New York) was used as the propellant.

Metered does of aerosolized insulin calibrated at 10 percent (10%) constancy of dose were delivered by means of a specially constructed mechanical pump valve (U.S. Pat. No. 4,511,069). This hand-held delivery device is uniquely nonvented so that the sterility of the solution in the aerosol container is maintained indefinitely.

Diabetic subjects were dosed with between 0.56 to 1.2 units insulin/kg body weight depending upon factors such as individual sensitivity, weight of the diabetic subject and the size/composition of the meal consumed.

Blood was taken from each subject every 15 minutes with plasma glucose being measured on a Yellow Springs glucose analyzer (YSF 23A). The serum insulin level was determined by radioimmunoassay with use of antibody-coated insulin-assay tubes from Micromedic (Horsham, Pa.).

| Test | Surfactant | % Conc. | Minutes[a] | Dosage U/Kg[b] | % BGR[c] |
|---|---|---|---|---|---|
| 1 | N-9 (100%) | 0.25%[d] | 60 | 1.2 | 45.4 |
| 2 | N-9 (100%) | 0.75%[d] | 45 | 0.56 | 69.6 |
| 3 | P80/N-9 (50:50%) | 0.50% | 75 | 1.2 | 37.9 |
| 4 | P80/N-9 (25:75%) | 0.10% | 30 | 1.0 | 14.0 |
| 5 | P80/N-9 (25:75%) | 0.25% | 60 | 1.2 | 51.5 |
| 6 | P80/N-9 (25:75%) | 0.50% | c | 1.0 | 61.0 |
| 7 | P80/N-9 (25:75%) | 0.50% | 30 | 1.1 | 59.2 |
| 8 | P80/N-9 (10:90%) | 0.50% | 45 | 0.81 | 47.0 |
| 9 | P80/N-9 (10:90%) | 0.75% | 30 | 1.2 | 57.9 |

Notes:
[a]Time required for lowest blood glucose level.
[b]Level of modified insulin inhaled based on subjects bodyweight.
[c]% reduction of lowest BGR.
[d]Nasal irritation reported by the subject.

EXAMPLE IV

The nasal spray solution of insulin was prepared and the subjects dosed as described in Example III.

Blood glucose values were measured as described in Example III.

| Surfactant | % Conc. | Units/Kg Insulin Dose | Blood Glucose Values/Min.[a] | | | | |
|---|---|---|---|---|---|---|---|
| | | | 0 | 30 | 45 | 60 | 75 |
| P80/N-9 (50:50%) | 0.50 | 1.0 | 95 | 84 | 72 | 61 | 59 |
| P80/N-9 (25:75%) | 0.25 | 1.0 | 99 | 73 | 57 | 48 | 54 |
| | 0.50 | 1.0 | 94 | 58 | 53 | 58 | |
| | 1.0 | 1.0 | 73 | 46 | 39 | 45 | |
| P80/N-9 (10:90%) | 0.25 | 1.0 | 86 | 36 | 55 | 69 | |
| | 0.50 | 1.0 | 83 | 60 | 44 | 50 | |
| | 0.75 | 1.0 | 76 | 32 | b | | |
| N-9 (100%) | 0.10[d] | 1.0 | 99 | 59 | 37 | 38 | |
| | 0.25[d] | 1.0 | 99 | 74 | 58 | 54 | |
| | 0.75[d] | 1.0 | 92 | 48 | 28 | 38 | |
| Control Insulin (No Surf.) | — | 1.0 | 84 | 85 | 80 | c | |

[a]Values of Blood Glucose after dosing
[b]Glucose too low-discontinued
[c]No change in Blood Glucose
[d]Nasal irritation reported Additional advantages and modifications of the invention disclosed herein will occur to those persons skilled in the art. Accordingly, the invention in its broader aspects is not limited to the specific details or illustrated examples described herein. Therefore, all departures made from the detail are deemed to be within the scope of the invention as defined by the appended claims.

I claim:

1. A method for intranasal administration of insulin with reduced nasal irritation which comprises administering a composition consisting essentially of a pharmaceutically effective amount of insulin, polysorbate-80 and nonoxynol-9 at a pH of between 6.8 to 7.2, and wherein the polysorbate-80 is at a concentration of between 0.01 to 0.5% by weight and the nonoxynol-9 is at a concentration of between 0.05 to 0.9% by weight.

2. A method according to claim 1 where the polysorbate-80 and nonoxynol-9 are present in a ratio of 10:90, weight-:weight.

3. A method according to claim 1 where the polysorbate-80 and nonoxynol-9 are present in a ratio of 25:75, weight-:weight.

4. A method according to claim 1 where the polysorbate-80 and nonoxynol-9 are present in a ratio of 50:50, weight-:weight.

5. A method according to claim 1 wherein the polysorbate-80 is at a concentration of 0.05% by weight and the nonoxynol-9 is at a concentration of 0.45% by weight.

6. A method according to claim 1 wherein the polysorbate-80 is at a concentration of 0.125% by weight and the nonoxynol-9 is at a concentration of 0.375% by weight.

7. A method according to claim 1 wherein the polysorbate-80 is at a concentration of 0.25% by weight and the nonoxynol-9 is at a concentration of 0.25% by weight.

* * * * *